United States Patent [19]

Caprihan

[11] Patent Number: 4,621,234
[45] Date of Patent: Nov. 4, 1986

[54] PULSED NMR FLOW MEASUREMENT

[75] Inventor: Arvind Caprihan, Albuquerque, N. Mex.

[73] Assignee: Lovelace Medical Foundation, Albuquerque, N. Mex.

[21] Appl. No.: 557,980

[22] Filed: Dec. 5, 1983

[51] Int. Cl.⁴ .............................................. G01V 3/00
[52] U.S. Cl. ..................................... 324/306; 324/307
[58] Field of Search ....................... 364/565, 566, 569; 324/306, 307, 312, 309; 128/653; 73/861.05, 861.07, 861.13, 861.16, 861.17

[56] References Cited

U.S. PATENT DOCUMENTS

| | | | |
|---|---|---|---|
| 2,960,650 | 11/1960 | Pinkley | 324/0.5 |
| 3,191,119 | 6/1965 | Singer | 324/0.5 |
| 3,419,793 | 4/1965 | Genthe et al. | 324/0.5 |
| 3,551,794 | 2/1968 | Vander Heyden | 324/0.5 |
| 3,553,728 | 1/1971 | Frank | 364/565 |
| 3,559,044 | 1/1971 | Vander Heyden | 324/0.5 |
| 3,802,263 | 4/1974 | Krechmery | 73/861.16 |
| 4,110,680 | 8/1978 | Bergmann | 324/306 |
| 4,339,716 | 7/1982 | Young | 324/309 |
| 4,520,828 | 6/1985 | Burl | 324/306 |

OTHER PUBLICATIONS

J. R. Singer "NMR Diffusion and Flow Measurements and an Introduction to Spin Phase Graphing", Journal of Phys. E: Sci. Instrument, vol. 11, (1978).
Grover, T. and J. R. Singer (1981), "NMR Spin-Echo Flow Measurements", J. Applied Phys., 42:938–940.
Singer, J. R. (1980), "Blood Flow Measurements by NMR of the Intact Body", IEEE Trans on Nuclear Science, 27:1245–1249.
Hemminga, M. A., P. A. de Jager and A. Sonneveld (1977), "The Study of Flow by Pulsed Nuclear Magnetic Resonance. I. Measurement of Flow Rates in the Presence of a Stationary Phase Using a Different Method", J. Magnetic Resonance, 27:359–370.
Garroway, A. N. (1974), "Velocity Measurements in Flowing Fluids by NMR", J. Physics D.: Applied Physics, 7:L159–L163.
Hemminga, M. A., P. A. de Jager (1980), "The Study of Flow by Pulsed Nuclear Magnetic Resonance. II. Measurement of Flow Velocities Using a Repetitive Pulse Method", J. Magnetic Resonance 37:1–16.

Primary Examiner—Reinhard J. Eisenzopf
Assistant Examiner—G. Peterkin
Attorney, Agent, or Firm—Nilsson, Robbins, Dalgarn, Berliner, Carson & Wurst

[57] ABSTRACT

A method for measuring the velocity of a fluid in a conduit, for example, blood in a blood vessel, using pulsed nuclear magnetic resonance, in which velocity is derived from measuring the mean instantaneous frequency of FID or spin echo signals. A feedback loop is used to monitor the velocity of the fluid and to generate either FID or spin echo signals depending upon the fluid velocity and/or decay of the FID signal. Radio frequency pulses are applied to suitable static axial magnetic gradients to obtain flow measurement from within a specific volume.

15 Claims, 6 Drawing Figures

PULSED NMR FLOW MEASUREMENT

BACKGROUND AND SUMMARY OF THE INVENTION

An object of the present invention is to provide an improved method using nuclear magnetic resonance (NMR) for measuring the flow of fluid in a conduit, more particularly, to measure the flow of blood in a subject, either separately from or in the course of NMR tomographic examination.

The use of NMR to measure blood flow appears to be virtually a noninvasive technique and relies upon detecting the magnetization of hydrogen protons in the blood. Blood protons retain their magnetization direction for an average time of about 0.7 seconds, during which time a free induction decay (FID) signal corresponding to the magnetization can be detected and utilized in a variety of schemes to provide information about the velocity of the blood flow. A static, homogenous magnetic field is established in the region of interest and a radio frequency (R.F.) pulse is applied having a frequency equal to about the Larmor frequency of the paramagnetic fluid. The Larmor frequency is that frequency at which the vectors of the magnetic moments of the nuclei freely precess in the magnetic field. The theoretical tracking time for the FID signal is equivalent to $T_1$ the classical relaxation time, i.e., the time during which the protons recover from the induced magnetization to the static magnetization. However, the decay of the FID signal is limited by other factors. It is dependent upon the relaxation time constant $T_2$ (a constant that is a property of the fluid resulting in nonuniformity of the precessing protons and affecting the total magnetic moment), the magnetic field gradient, inhomogeneity of the static magnetic field, the fluid velocity and the length of the receiver coil. During the course of decay of the FID signal, one can apply a train of 180° pulses to cause the precessing protons to "flip", yielding successive spin echo pulses which decrease in amplitude.

A review of blood flow measurement in the context of NMR imaging is contained in a paper by Singer: "Blood Flow Measurements by NMR of the Intact Body", IEEE Trans. on Nuclear Science (1980), 27:1245-1249. He describes a pulsed NMR experiment for velocity measurement of flowing fluids in which an R.F. pulse is applied in the presence or absence of a static magnetic field gradient. The received signal can be a FID signal or spin echoes can be measured if a suitable series of R.F. pulses is applied. In a paper by Grover and Singer: "NMR Spin-Echo Flow Measurements", J. Applied Phys. (1971), 42:938-940, a magnetic field gradient was applied in the direction of fluid flow with an R.F. pulse train 90° - t - 180°. where t is the time between the R.F. pulses. The amplitudes of the resulting spin echoes were measured as a function of t and the velocity distribution function derived from this information.

Garroway, in "Velocity Measurements in Flowing Fluids by NMR", J. Phys. D: Applied Phys. (1974), 7:L159-L163 suggested two methods for velocity measurement. He applied the magnetic field gradient perpendicular to the flow with a 90° - t - 90° R.F. pulse sequence. He measured the FID signal after the second pulse and showed that information on the spatial velocity profile can be obtained. His second method was similar to that of Grover and Singer. He applied the magnetic field gradient in the direction of flow and a ($90_0$- (t) - $90_{90}$) R.F. pulse sequence. Information on the flow of velocity distribution was obtained from the amplitudes of the spin echoes.

In a paper by Hemminga et al: "The Study of Flow by Pulsed Nuclear Magnetic Resonance. I. Measurement of Flow Rates in the Presence of a Stationery Phase Using a Difference Method", J. Magnetic Resonance (1977), 27:359-370, a Carr-Purcell-Meiboom-Gill (CPMG) pulse sequence to generate spin echoes was used in the absence of magnetic field gradients and the mean velocities were measured from the amplitude of the spin echos. In a subsequent paper by Hemminga: "The Study of Flow by Pulsed Nuclear Magnetic Resonance. II. Measurement of Flow Velocities Using a Repetitive Pulsed Method", J. Magnetic Resonance (1980), 37: 1-16, R.F. pulsed sequences were used in the presence of magnetic field gradients in the direction of flow. Velocity measurements were made using the amplitudes of the spin echoes.

Other methods for utilizing signals obtained during decay of the nuclear magnetic resonance of test fluid have been proposed. In Vander Hayden, U.S. Pat. No. 3,559,044, NMR is used to tag and detect a bolus to measure fluid flow. A tagging pulse is generated for each tagged bolus detected by a receiver coil, the period between successive tagging pulses defining a constant quantity of fluid passing through the conduit so that the number of pulses indicate the quantity of fluid flowing into the conduit. In Vander Hayden et al, U.S. Pat. No. 3,551,794, a signal responsive to the amplitude of the net magnetization of the fluid is used to measure flow, feedback being used to maintain a constant phase difference between the oscillators signal and the output signal. In Genthe et al Pat. No. 3,419,793 the number of pulses occurring in unit time is measured and is taken as proportional to the average fluid velocity. In Singer U.S. Pat. No. 3,191,119 a time-of-flight method is described in which the time elapsed between application of the excitation pulse and its detection is divided by the distance between the point of excitation and the point of detection to provide the flow rate.

A distinct drawback to all the foregoing methods of fluid velocity measurement is that they yield only the average velocity of the fluid. While such information is quite adequate for uniform or static systems, such as pipelines, and gives desirable information about the flow of blood, nevertheless average flow velocity does not adequately describe the physical conditions of the arteries and veins in the human body. For example, local variations in flow such as from artery blockages, from cholesterol buildup, the loss of elasticity and the like, and temporal variations from pulsations cannot be readily discerned using average velocity.

Furthermore, in any tubular vessel there is a spatial distribution between velocity along the inner surface of the walls and in the center of the vessel. Determining the spatial distribution of fluid velocity can yield important information as to the nature of the fluid flow, for example whether it is parabolic in shape, indicating laminar flow or nonparabolic, indicating turbulent flow. Because investigators have suspected there may be a link between turbulent arterial flow and artherogenesis, the matter has assumed a high degree of clinical interest. It would therefore be desirable to obtain not only information about the velocity of blood flowing in an artery or vein, but also information as to the velocity distribution as the blood progresses through the vessel.

In accordance with the present invention one readily obtains such information by measuring the instantaneous frequency of the nuclear magnetic resonance, either of the FID signal or of the spin echo signal, and deriving velocity information from the rate of change of the mean instantaneous frequency. Selection of the FID signal or spin echo pulse is governed by a feedback loop which monitors the velocity of the fluid and generates either signal depending upon the fluid velocity and/or decay of the FID signal. In addition, R.F. pulses are applied to suitable static axial magnetic gradients to obtain flow measurement from within a specific volume.

It will be appreciated that the methods provided herein can be used in fields other than measurement of the flow of blood in an artery or vein. More broadly, a method is provided for measuring the flow of fluid in a conduit, the atomic nuclei of at least one component of the fluid displaying a nuclear magnetic moment and angular momentum. As an initial step, a first, static, substantially homogenous axial magnetic field is established within the conduit and a magnetic field gradient is applied along the direction of flow of the fluid sufficient to induce nuclear paramagnetization in the fluid. An R.F. pulse having a frequency equal to the Larmor precession frequency of the nuclei of the element at the field intensity of the magnetic field is applied to a region within a conduit so as to alter the nuclear magnetization within a bolus of the fluid, thereby tagging the bolus with respect to fluid preceding and following the bolus. The frequency of nuclear magnetic resonance of the atomic nuclei of the element in the bolus, whether it be FID or spin echo, is measured over predetermined periods of time to obtain for each period of time the mean instantaneous frequency of the nuclear magnetic resonance. Velocity of the fluid is then derived from the rate of change of the mean instantaneous frequency.

In a particular implementation, a narrow band 90° R.F. pulse is applied in the presence of $G_y$. $G_y$ is the magnetic field gradient in the desired direction of the flow measurement. An appropriate gradient reversal of $G_y$ is then necessary for echo formation. This is followed by switching the field gradient along an orthogonal z-axis ($G_z$) and applying a selective, narrow band 180° pulse after time $t_{\frac{1}{2}}$. After another time $t_{\frac{1}{2}}$ the field gradient is switched along the x-axis ($G_x$) and a selective, narrow band 180° pulse is applied after time $t_{2/2}$. Then, after a delay of $t_{2/2}$ the field gradient is switched back to $G_y$ and FID and spin echoes can be measured for velocity determination. In this manner, the nuclear magnetization is altered within a selected volume of the fluid, thereby tagging that volume with respect to the fluid preceding and following the volume.

Initially, a 90° R.F. pulse is applied to generate a FID signal, but because of the decay of the FID signal, the velocity information can only be obtained for some finite time and then a fresh R.F. pulse, selected to generate a FID signal, must be applied, i.e., a new 90° R.F. pulse. Such a new pulse would be effective only if the magnetization at the selected region has reached the static equilibrium value. If the velocity of the fluid is sufficiently high then new material will have moved within the receiver coil and another 90° R.F. pulse can be applied. However, if the velocity is low a new FID signal cannot be generated because the protons have not reached static magnetization. In accordance with a further embodiment of this invention, at that time, as long as there has not been full $T_2$ decay, a series of 180° R.F. pulses can be applied to generate a train of spin echo signals. On the other hand, if the FID signal has decayed due to true $T_2$, then one would have to wait for a period of time, depending on $T_1$ until the next 90° R.F. pulse can be applied to generate a new FID signal. In accordance with a still further embodiment of the present invention, a method utilizing computerized feedback is provided to analyze the instantaneous position of the selected sample and amplitude of the generated signal, and suitably control the timing and phase of the next pulse.

More particularly, when magnetization of the tagged fluid has not reached a static value (i.e., within a time less than the spin-lattice relaxation time) a series of steps is conducted in which 180° radio frequency pulses are applied to generate spin echo signals which are monitored and measured to obtain periodic samples of their mean instantaneous frequency deriving the velocity of the fluid from the rate of change of the mean instantaneous frequency and determining as well the amplitude of the signal. When the maximum amplitude of the spin echo signal is less than a predetermined threshold level a determination is made as to whether sufficient fluid flow has occurred or sufficient time has passed to reinstitute a 90° R.F. pulse to generate another FID signal.

Accordingly, the present invention incorporates several improvements in the utilization of nuclear magnetic resonance to measure the flow of a fluid. One improvement of the FID or spin echo signals and deriving the velocity of the fluid from the rate of change of the mean instantaneous frequency. Another improvement is feedback of the timing and selection of the R.F. pulse to generate a series of spin echo signals alternating with FID signals. A still further improvement is the utilization, in conjunction with the measurement of the mean instantaneous frequency, of a sequence of magnetic field gradients and radiofrequency pulses to define a selected volume from within which the frequency is measured.

DETAILED DESCRIPTION

Although the present invention will be exemplified with respect to the measurement of the flow of blood in a blood vessel, it will be appreciated that the concepts and principals are directly applicable to the measurement of any fluid composed of or carrying atomic nuclei that display nuclear magnetic moment and angular momentum.

Figure 1:
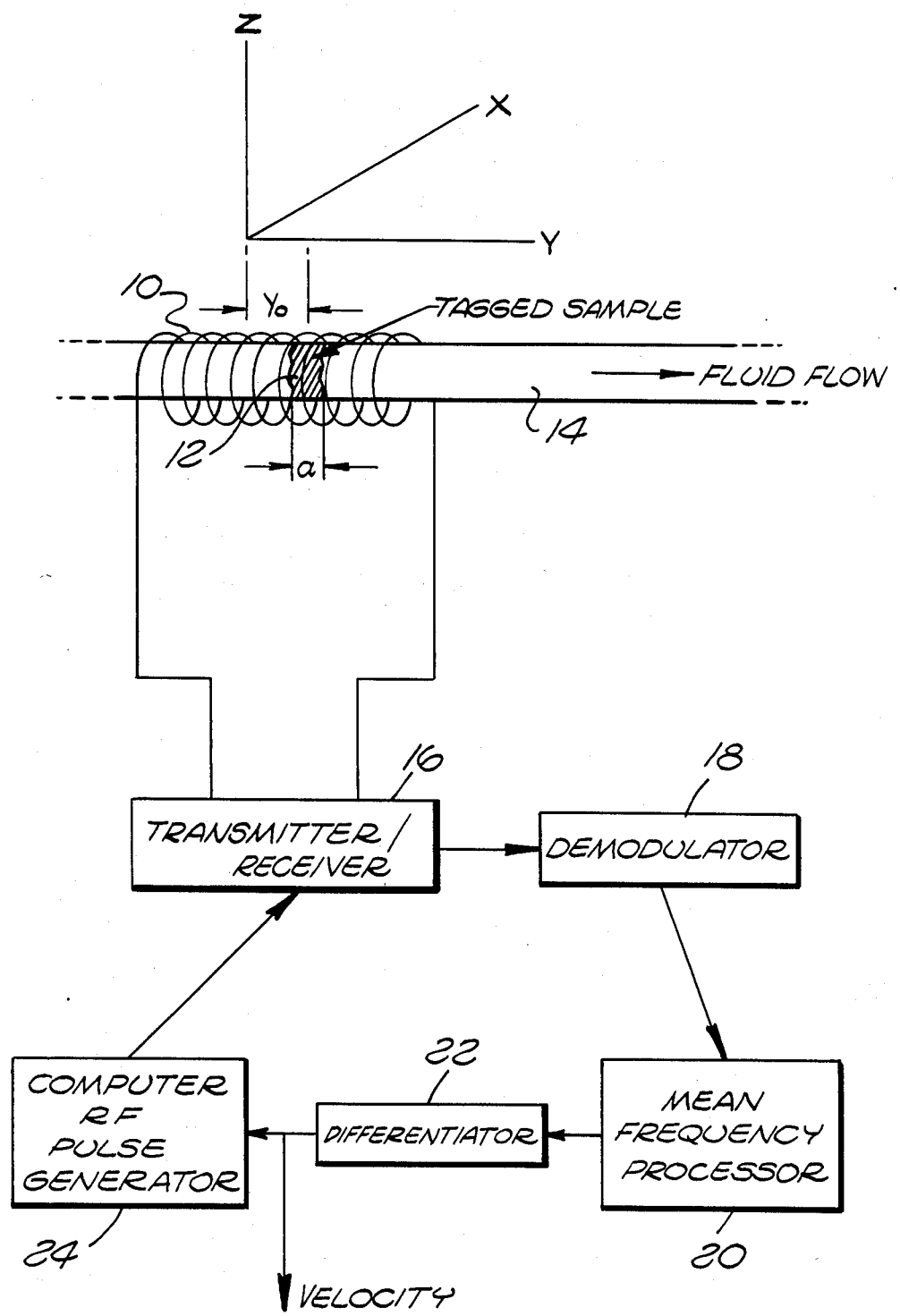
FIG. 1 is a schematic and block diagram showing an NMR system for flow measurement usable in accordance with the present invention.

A schematic diagram of apparatus that can be utilized in the present invention is shown in FIG. 1. A static, homogenous field B is applied along the x axis. The direction of flow is along the y axis. A static magnetic field gradient is also applied along the y axis, and is given by:

$$B = (B_o + G_y y)\vec{i}$$

where $B_o$ is the static field and $G_y$ is the magnetic field gradient along the y-axis. A common transmitter/receiver coil 10 with the coil axis along the y-direction is used. Of course, the coil depicted in FIG. 1 is only schematic in showing the relationship of the field components, sample and coil. A narrow band, selective R.F. pulse of frequency $\gamma G_y y$ is applied in the presence of the magnetic field gradient $G_y$ along the y-axis where $\gamma$ is the gyromagnetic ratio. This pulse will select a slice of width "a" within which the proton spin magnetization has rotated through 90° and outside of which spin magnetization has not changed. In practice, a precise boundary for the slice is not obtained and there is some distortion due to imperfect slice selection. The pulse thus tags a narrow bolus 12 of the fluid in the conduit 14. As will be described subsequently, other pulses are used to select a specific volume within the conduit, but for simplicity have been omitted from FIG. 1.

As will also be described in more detail hereinafter, a FID signal is generated which is sensed by the same transmitter/receiver coil 10 through a transmitter/receiver 16. The FID signal can be phase-sensitive, quadrature-demodulated at 18, passed through a velocity estimator which consists of a mean frequency processor 20 and its output differentiated at a differentiator 22. A number of different hardware realizations can be used for the mean frequency processor 20 and the differentiator 22. For example, one can use short term Fourier transforms to estimate the mean frequency of the moving protons, or a zero crosser whose output voltage is proportional to the instantaneous root mean square value of the frequency can be used. The differentiator can be implemented digitally. In any case, these are commonly available hardware components. As will be described in more detail hereinafter, a feedback loop can be established with a computer and radio frequency pulse generator at 24 connected to the transmitter receiver, to operate simultaneously with the generation of velocity information.

Figure 2:
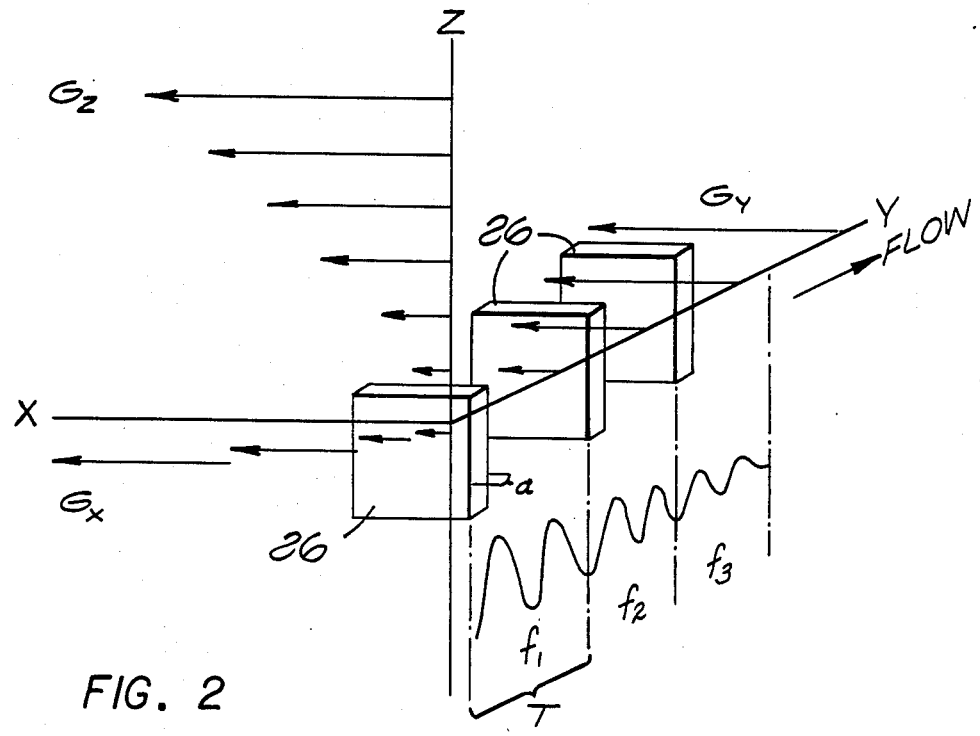
FIG. 2 is a vector diagram displaying the orientation of the various magnetic field gradients used in the present invention and having overlaid thereon the flow of movement of selected volumes of fluid and decaying nuclear magnetic resonance signal (the three magnetic fields are not applied simultaneously)

Referring to FIG. 2, there is illustrated the three magnetic field gradients. The three field gradients are applied sequentially and are shown together for purposes of illustration. The direction of the three fields is along the x-axis, the direction of the static homogenous field. The direction of the increase is along the three co-ordinates axis. One of the fields, $G_y$ is collinear with the desired direction of flow measurement. A selected volume of width 'a' is shown at successive periods of time t flowing along the y-axis.

Figure 3:
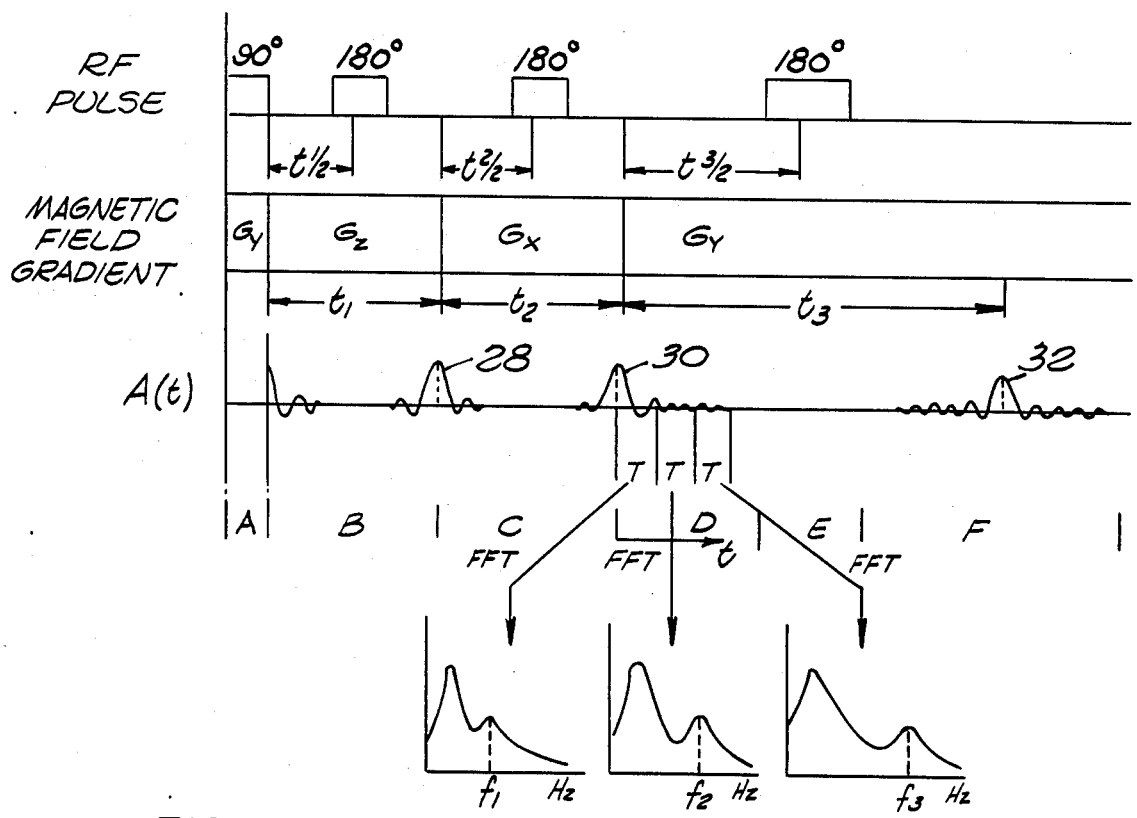
FIG. 3 is a graphical illustration of the pulse sequence for volume selection and flow measurement.

Referring additionally to FIG. 3, the pulse sequence used for volume selection and flow measurement is shown in which:

"A" represents the magnetic field gradient $G_y$ along the flow direction.
"B" and "C" indicate volume selection gradients and R.F. pulses 28 and 30.
"D" indicates the FID readout in the presence of magnetic field gradient $G_y$.
"E" indicates the application of a 180° R.F. pulse to generate a spin echo signal.
"F" indicates the spin echo signal 32.

A narrow band 90° R.F. pulse is applied in the presence of the magnetic field gradient $G_y$ (a gradient reversal of $G_y$ will be necessary for echo-formation, which is not indicated in FIG. 3). This is followed by switching the field to $G_z$, a magnetic field in the z-direction. After a suitable time, $t_{\frac{1}{2}}$, a selective, narrow band R.F. pulse of 180° is applied. This pulse could be either of the CPMG type or the HAHN type (both types of pulses are used for generating spin echoes). After another time, $t_1/2$, the gradient is changed to $G_x$. Again, after some time, $t_2/2$, the magnetic field gradient is switched back to $G_y$. By using phases A, B and C as shown in FIG. 3, a volume 26 (FIG. 2) is selected from which flow is measured.

Referring to the pulse sequence in more detail, but for the present discussion omitting phases B and C used for volume selection, the FID signal is observed in the presence of the magnetic field gradient $G_y$ (the intensity of which can be different from the field applied during slice selection). At this point, as indicated above, the FID signal is phase-sensitive, quadrature-demodulated. The output V(t) can be expressed as:

$$V(t) = A(t) + iB(t),$$

$$\alpha \int_{v_1} \rho(s,y,z)m(x,y,z)\exp(k(-G_y\bar{y}t)dxdydz +$$

$$\int_{v_2} \rho(x,y,z)m(x,y,z)\exp(i\{-\gamma G_y\bar{y}t - \gamma G_y vt^2/2\})dxdydz$$

where A(t) is the output of the quadrature demodulator with the in-phase reference and B(t) the output with quadrature reference. The integrals are present to indicate one region with no flow and the other region with plug flow. The method is explained for plug flow. The distribution of protons with different velocities would have to be taken into account for other flow profiles. We will assume that:

$$\rho(x,y,z) = \text{constant}$$

$$m(x,y,z) = 1 \text{ for } \bar{y} - a/2 < y < \bar{y} + a/2,$$

$$= 0 \text{ otherwise.}$$

This corresponds to ideal slice selection of width a. Then $$A(t)\alpha(\sin(ct)/ct))*\exp(-t/T_2)[A1*\cos(\gamma G_y\bar{y}t)+A2*\cos(\gamma G_y\bar{y}t+\gamma G_y vt^2/2)],$$

where $$c = \gamma G_y a/2. \quad (1)$$

B(t) is proportional to an expression like eq (1) with cosine terms replaced by sine terms. The ratio of A2 to A1 is equal to the ratio of the number of protons with velocity v to the number of stationary protons.

The velocity, v, can be estimated by studying the rate of change of the mean instantaneous frequency above the slice selection frequency of $\gamma G_y y$. The mean instantaneous frequency above $\gamma G_y y$ of the signal in eq (1)

would be $\gamma G_y vt$ and its derivative is $\gamma G_y v$. Since $\gamma$ and G are known the velocity can be calculated from the derivative.

In a particular embodiment of the invention the mean frequency estimator is implemented by dividing the total observed FID into subsections of T milliseconds each and calculating the Fourier transform of each section. For the measurement of blood flow, T is advantageously in the range of about 5 milliseconds to about 40 milliseconds with 30 milliseconds being typical. The peaks corresponding to the protons in motion are separated, and their mean frequency estimated. The rate of change in the mean frequency provides an estimate of the velocity. This method has the advantage of being sensitive to the direction of flow, allowing one to separate simultaneous flow present in opposite directions within a selected volume, for example, as may be the case with arteries and closely placed veins. It also enables one to estimate the velocity distribution of the protons. An alternative, simpler implementation, but without the advantage of sensitivity to the flow direction, is the use of a zero-crosser as a mean frequency estimator.

The decay of the FID signal is dependent on the relaxation time constant $T_2$, magnetic field gradient, inhomogeneity of the static magnetic field, fluid velocity and the length of the receiver coil. Thus the velocity information can only be obtained for some finite time and then a fresh selective R.F. pulse has to be applied. The new 90° R.F. pulse will be effective only if the magnetization at the selected region has reached the static equilibrium value. If the velocity is sufficiently high then new protons will have moved within the receiver coil and a 90° R.F. pulse could be applied. In accordance with an embodiment of the present invention, if the velocity is low and the FID signal has decayed because of magnetic field inhomogeneity, then a 180° R.F. pulse is applied to generate a spin echo and followed by similar processing. Under these conditions a train of spin echoes are generated. On the other hand if the FID signal has decayed due to true $T_2$, then one would have to wait for some time, dependent on $T_1$ until the next 90° R.F. pulse can be applied. As indicated at 24 in FIG. 1, and as described in more detail hereinafter, a computer is used to analyze the instantaneous position of the selected sample and suitably control the timing of the next pulse.

Referring again now to the additional phases B and C in FIG. 1, if time is measured from the beginning of phase D, the signal A(t) will be proportional to:

$$A(t)\gamma\exp(-(t1+t2)/T_2*\{\sin(ct)/ct\}*\{A1*\cos(G_y\bar{y}t)+A2*\cos(\gamma G_y(\bar{y}+v*t1+v*t2)t+\gamma G_y vt^2/2)\}$$

This equation has the same structure as eq (1) and similar processing will yield the velocity data.

Figure 4:
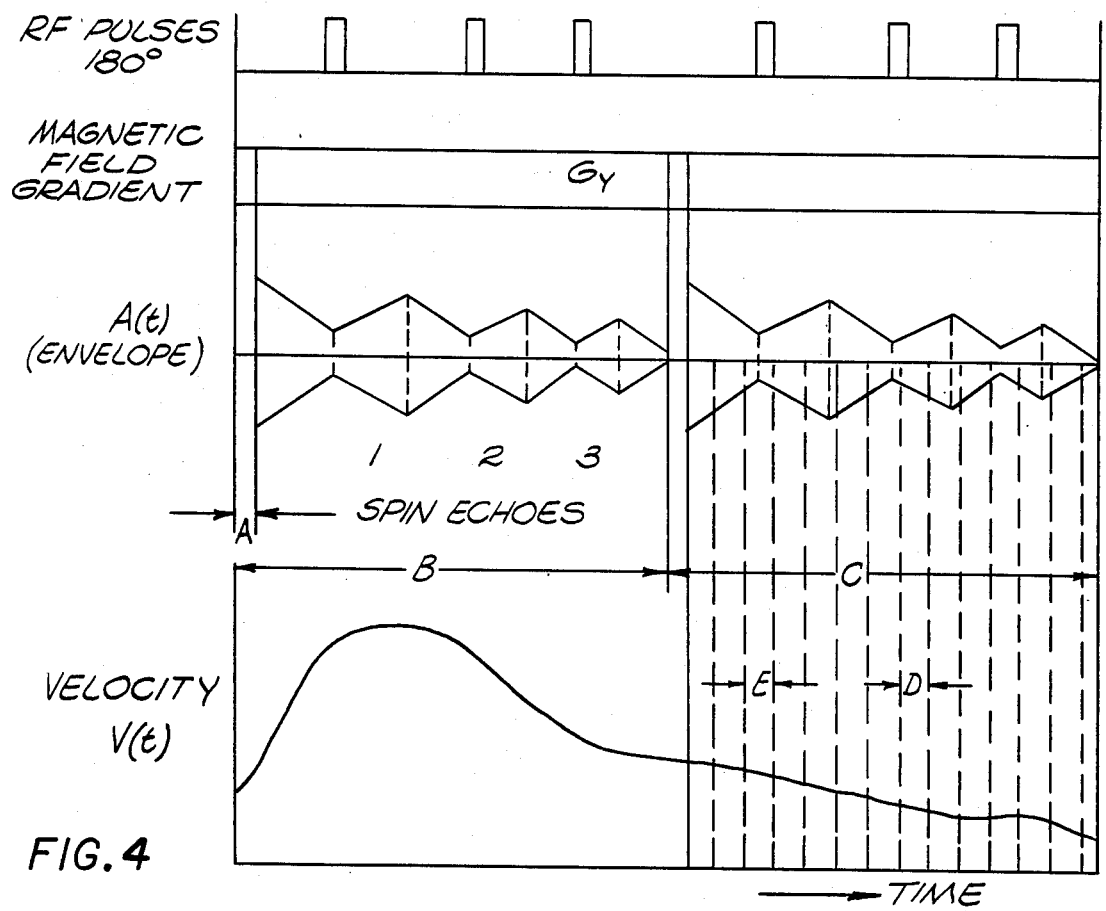
FIG. 4 is a graphical illustration of spin echo signal acquisition sequences as used herein.

Referring to FIG. 4, two typical signal acquisition sequences are shown:

"A" indicates a volume selection interval.

"B" indicates a signal collection sequence of about 250 milliseconds.

"C" indicates the next signal collection sequence.

"D" indicates a subsection of the FID and spin echos for velocity estimation; this sets the sampling rate of the velocity.

"E" indicates a section where the signal cannot be measured due to the application of the 180° R.F. pulse.

EXAMPLE

Referring now to a specific embodiment and implementation, the calculation of the various parameters is dependent on the measurable duration of the FID signal or the spin echoes in the presence of magnetic field gradients and the inhomogeneity of the static magnetic field. Since all the calculations are dependent on this duration, it will be discussed first.

The FID signal, x(t) decays exponentially and its duration will be defined in reference to the number of bits of the a/d converter. Consider that the FID is normalized so that:

$$\max(x(t))=1,$$

then the duration of x(t) will be the largest time, TD such that:

$$x(t) < \tfrac{1}{2}^p, \text{ for } t > TD \text{ and a given p}.$$

If $x(t)=\exp(-t/100)$ and $p=8$, then $TD=554$. (Note that p is not the number of bits of a/d converter but the number of bits above which the signal is stronger than the noise).

If inhomogeneity of the magnetic field is neglected then the FID signal after phase sensitive, quadrature demodulation will be proportional to:

$$A(t)\alpha[\sin(ct)/ct]*\exp(-t/T_2)*\cos(\gamma G_y yt + \gamma G_y vt^2/2)$$

where $c=\gamma G_y a/2$ and "a" is the width of the slice selected in the y-direction. The function that will be used for calculating the duration is:

$$x(t)=[\sin(ct)/ct]*\exp(-t/T_2).$$

If there is a magnetic field inhomogeneity of DB Gauss over the selected volume, then it can be taken into account if a new effective $T_2^*$ is defined by:

$$1/T_2^* = 1/T_2 + \gamma DB/2.$$

The magnetic field inhomogeneity is usually specified in terms of parts per million (PPM), over a given volume. Assuming that it is specified over a volume of 1000 cu.cm. and that DB is proportional to the volume, then:

$$DB = PPM*BO*SV/(10^6*10^3)$$

where $B_o$ is the static field and SV the sample volume. If $PPM=10$, $B_o=10000$ Gauss and $SV=4$ cu.cm. then $DB=0.0004$ Gauss.

Since the spin echoes will be generated at a delay of TS from the time FID is measured, their maximum amplitude will have decayed in this time TS by the time constant $T_2$. The duration of the spin echoes is calculated from:

$$x(t) = [\sin(ct)/ct]*\exp(-t/T_2^*)*\exp(-TS/T_2).$$

Thus the measurable duration of the spin echoes reduces as TS is increased. The duration of the signal (TD), is a function of magnetic field gradient (G), the slice width in its direction (a), the magnetic field homogeneity (PPM), the sample volume (SV), the transverse relaxation time constant ($T_2$), the delay in the signal (TS) and the number of effective bits of the A/D conversion (p). Thus:

$$TD = f(G, a, PPM, SV, T_2, TS, p). \quad (1)$$

The velocity is estimated by taking two adjacent subsections of FID, say time T long and calculating the mean frequency of the protons in motion and calculating its rate of change. If the velocity is v cm/s then in time T the mean change in frequency will be approximately equal to:

$$DF = \gamma GvT/2\pi \quad (2)$$

Since the length of the section was T, the minimum resolvable frequency by FFT is 1/T. If this is equated to eq(2), we get:

$$VRES = 2\pi/(\gamma G*T*T).$$

The value of T cannot be increased indefinitely to improve the resolution, as it is dependent on G which limits the duration of the signal. The value of T also controls the sampling frequency of velocity data. The sampling frequency is given by:

$$FV = 1/T.$$

These calculations have assumed that FV is greater than 30 Hz and T is not greater than half the duration of the FID. This ensures a sampling rate for the velocity of at least 30 Hz and from a FID at least one estimate of the velocity is available.

Similarly, there is a limit on the maximum velocity detectable in time T. Suppose the sampling interval of FID and the spin echoes to be TS sec. Then by the Nyquist condition (which relates the sampling rate to the maximum frequency in the signal) the maximum frequency in the signal is FMAX:

$$FMAX = \tfrac{1}{2}*TS.$$

Equating this to eq(2), the maximum velocity detectable is:

$$VMAX = 2\pi*FMAX/(\gamma GT).$$

In practice this limit is lowered by a factor of 8, and if the maximum velocity of interest is limited to 100 cm/s, then:

$$FMAX = 8*\gamma*G*T*VMAX/2\pi$$

The duration between spin echoes has not been considered constant. This is because the duration of subsequent spin echoes reduces and it is more efficient to generate them more rapidly. Thus, it is assumed that the duration between spin echoes is some multiple of T plus 2ms and is adjusted so that the signal can be measured almost continuously. After the duration of the spin echo becomes less than T, it cannot be usefully measured and a fresh volume selection procedure is started.

Using computer simulation to vary $T_2$, PPM, p and the magnetic field gradients during selection and during readout, their effect on the following has been studied:
(a) Time duration for volume selection
(b) Duration of FID
(c) Sampling frequency for the velocity
(d) Velocity resolution
(e) Time between spin echoes
(f) Duration of spin echoes
(g) Number of spin echoes
(h) Total time for signal collection Pertinent findings are presented in Tables 1, 2 and 3. Tables 1 and 2 show the effect of increasing PPM from 10 to 20 and Tables 1 and 3 show the effect of increasing p from 8 to 10. A higher value of PPM reduces the signal duration and increases the value of VRES. A higher value of p reduces the value of VRES.

A suitable value of G is 0.1 Gauss/cm which results in a VRES = 2.38 cm/s, with $T_2$ = 100 ms, a = 1 cm, Vol = 4.0 c.cm, p = 8 and PPM = 10. Measuring flow at 10 cm/s ensures that in 200 ms the protons will have moved 2 cm. which is twice the slice width.

Figure 5:
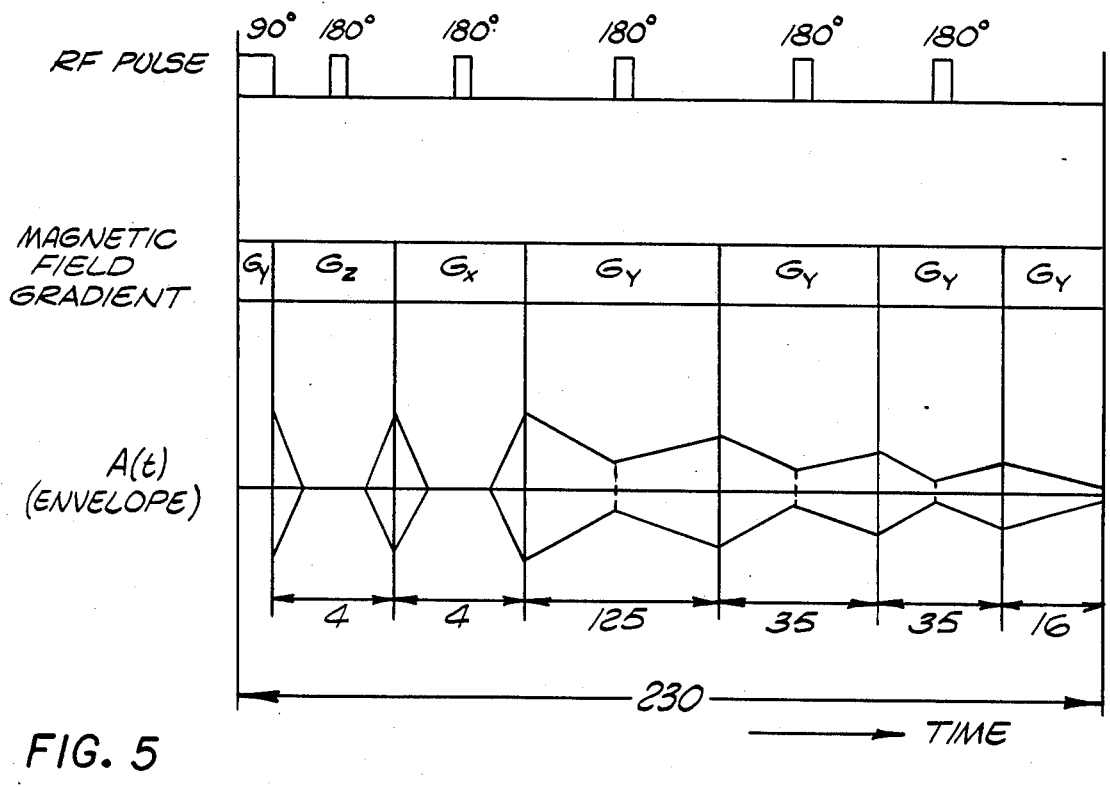
FIG. 5 is a graphical illustration of the timing of R.F. pulse sequences and magnetic field gradients utilized in the present invention.

Referring to FIG. 5 the timing of the R.F. pulse sequences is shown. After the initial application of $G_y$ and a 90° pulse gradient reversal of $G_y$ is needed for echo formation which is not indicated in FIG. 5. Gx and Gz each can be 1 Gauss/cm and Gy can be 0.1 Gauss/cm. The sampling frequency of the FID can be 22 KHz. The flow direction is assumed to be along the y-axis. The slice width along the y-axis is 1 cm. All the R.F. pulses are narrow band and can be amplitude modulated by a suitable Gauss function to give narrow slice selection with no side lobes. The volume selection intervals for z-slice and x-slice are 4 ms each. The slice width is 2 cm in either direction, giving a selected volume of 4 $cm^3$.

TABLE 1

| G Gauss/cm | 0.025 | 0.05 | 0.075 | 0.1 | 0.25 | 0.5 |
|---|---|---|---|---|---|---|
| Duration of FID (ms) | 117 | 92 | 74 | 63 | 40 | 21 |
| FV (Hz) | 30 | 30 | 30 | 31.74 | 50 | 95.23 |
| VRES (cm/s) | 8.46 | 4.23 | 2.82 | 2.38 | 2.35 | 4.26 |
| Sampling frequency of FID (khz) | 5.68 | 11.36 | 17.02 | 21.46 | 34.06 | 35.76 |
| No. of samples in a FID | 664 | 1044 | 1260 | 1351 | 1362 | 750 |
| No. of spin echoes | 3 | 4 | 3 | 3 | 4 | 9 |
| Total measurement time (ms) | 323 | 292 | 251 | 211 | 179 | 182 |

$T_2$ = 100 ms, a = 1 cm, vol = 4.0 cm, p = 8 and PPM = 10

TABLE 2

| G Gauss/cm | 0.025 | 0.05 | 0.075 | 0.1 | 0.25 | 0.5 |
|---|---|---|---|---|---|---|
| Duration of FID (ms) | 97 | 77 | 61 | 58 | 27 | 21 |
| FV (Hz) | 30.0 | 30.0 | 32.8 | 34.5 | 74.07 | 95.24 |
| VRES (cm/s) | 8.46 | 4.23 | 3.37 | 2.79 | 5.16 | 4.26 |
| Sampling frequency of FID (khz) | 5.68 | 11.36 | 15.58 | 19.74 | 22.98 | 35.76 |
| No. of samples in a FID | 550 | 874 | 950 | 1145 | 620 | 75 |
| No. of spin echoes | 4 | 4 | 3 | 3 | 10 | 9 |
| Total measurement time (ms) | 325 | 292 | 235 | 224 | 230 | 182 |

$T_2$ = 100 ms, a = 1 cm, vol = 4.0 cm, p = 8 and PPM = 20

TABLE 3

| G Gauss/cm | 0.025 | 0.05 | 0.075 | 0.1 | 0.25 | 0.5 |
|---|---|---|---|---|---|---|
| Duration of FID (ms) | 182 | 148 | 130 | 119 | 84 | 59 |
| FV (Hz) | 30.0 | 30.0 | 30.0 | 30.0 | 30.0 | 33.9 |
| VRES (cm/s) | 8.48 | 4.23 | 2.82 | 2.11 | 0.846 | 0.54 |
| Sampling frequency of FID (khz) | 5.68 | 11.36 | 17.02 | 22.71 | 56.76 | 100.46 |
| No. of samples in a FID | 1033 | 1680 | 2213 | 2701 | 4767 | 5927 |
| No. of spin echoes | 4 | 4 | 4 | 3 | 2 | 2 |
| Total measurement time (ms) | 459 | 425 | 392 | 323 | 221 | 167 |

T = 100 ms, a = 1 cm, vol = 4.0 cm, p = 10 and PPM = 10

Figure 6:
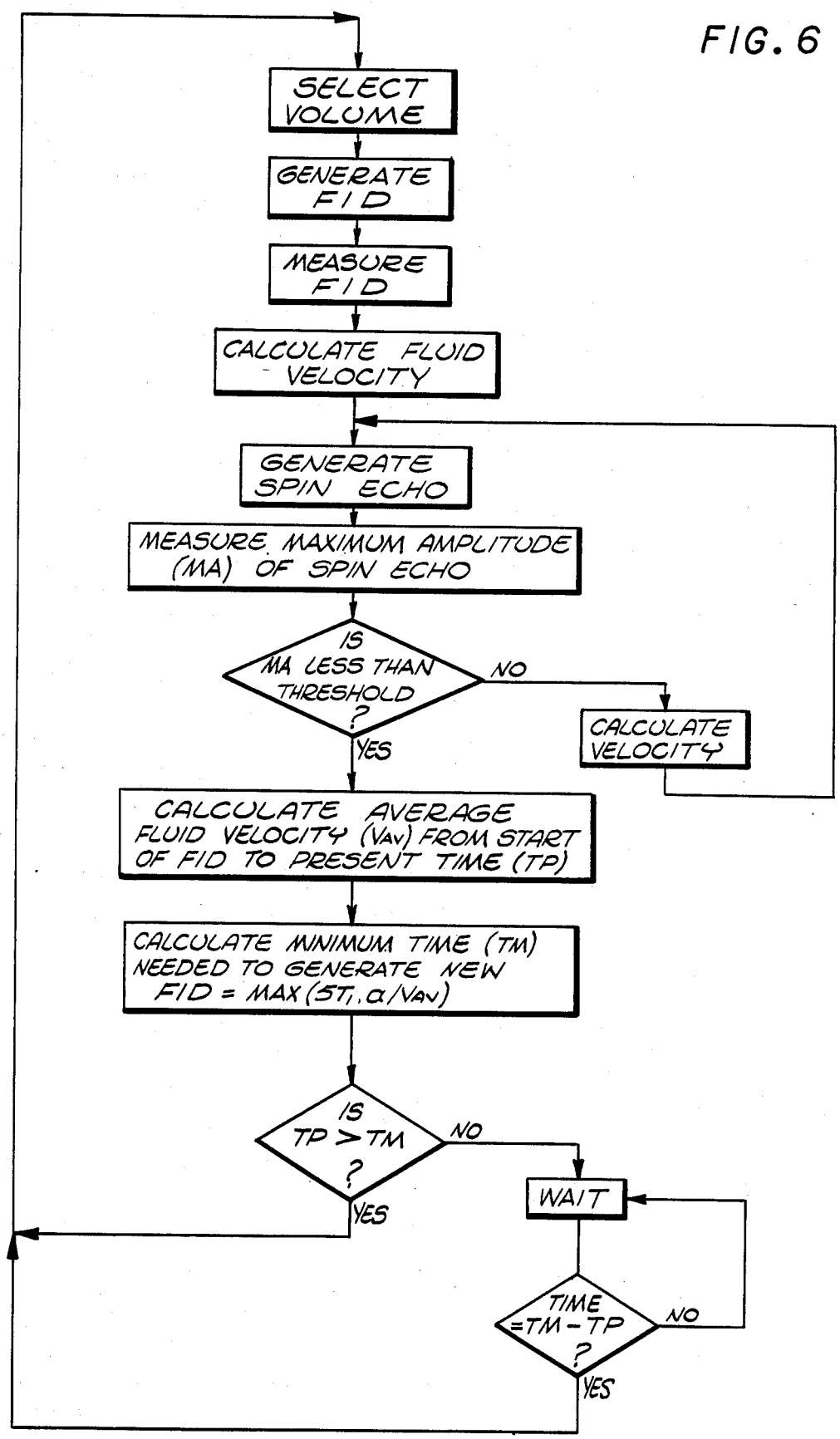
FIG. 6 is a flow chart of the steps utilized for feedback control of the pulse sequences and magnetic field gradient utilized in the present invention.

Referring to FIG. 6, a flow chart is shown for the steps used in feedback control of the phase and timing of the R.F. pulse. There are two objectives to feedback control. One is to generate spin echoes for as long as it is possible to derive velocity information from them. This is done by monitoring the maximum amplitude of the spin echo and stopping when it is below a threshold. The other is to reduce the time between successive FID signals to a minimum. This is done by monitoring the average velocity and using apriori information of the $T_1$ relaxation time constant for the fluid. Following the chart on FIG. 6, one selects a volume and generates the FID by an appropriate choice of the R.F. pulse sequence and magnetic field gradients. The FID is then measured and the fluid velocity calculated from the data.

Next a spin echo signal is generated by an appropriate choice of the R.F. pulse sequence. The amplitude and mean instantaneous frequency of the spin echo signal is then measured. When the maximum amplitude is equal to or above the threshold value (for example, ½ in the previous example), the data is used to calculate the velocity of the fluid and an additional spin echo signal is generated. If the maximum amplitude is less than the threshold level, the average velocity of the fluid ($V_{AV}$) from the start of FID to the present ($T_p$) is calculated. In addition, the minimum time (Tm) needed to generate a new FID, i.e., $\max(5T_1, a/V_{AV})$, is calculated. As indicated in the chart this permits a mathematical determination of when it is appropriate to reinstitute FID signal generation. Stated another way, one determines the maximum time period as between (i) the time required for full free induction decay of the nuclear magnetic resonance and (ii) the time for the fluid to flow (at the average fluid velocity) a distance equal to the thickness of the volume in the direction of the magnetic field gradient. When the time lapse from the beginning of free induction decay of the nuclear magnetic resonance is greater than the maximum time period a new cycle of FID signal generation is started.

It should be understood that the above described arrangements are merely illustrative of the principles of this invention and that numerous modifications may be provided without departing from the scope of the invention.

I claim:

1. A method for measuring flow of fluid in a conduit, the atomic nuclei of at least one component of said fluid displaying a nuclear magnetic moment and angular momentum, comprising:

establishing a first static, substantially homogenous axial magnetic field within said conduit having a gradient along the direction of flow of said fluid sufficient to induce nuclear paramagentization in said fluid;

applying to a region within said conduit a radio frequency pulse having a first frequency about equal to the Larmor precession frequency of the nuclei of said element at the field intensity of said first magnetic field, whereby to alter the nuclear magnetization within a bolus of said fluid to thereby tag said bolus with respect to fluid preceding and following said bolus;

measuring the frequency of nuclear magnetic resonance of the atomic nuclei of said element in said bolus over predetermined periods of time to obtain for each period of time the mean instantaneous frequency of said nuclear magnetic resonance; and deriving the velocity of said fluid from the rate of change of said mean instantaneous frequency.

2. The method of claim 1 in which said radio frequency is applied under conditions to generate a free induction decay signal, said measured frequency resulting from free induction decay of said nuclear magnetic resonance.

3. A method for measuring flow of fluid in a conduit, the atomic nuclei of at least one component of said fluid displaying a nuclear magnetic moment and angular momentum, comprising:

establishing a first static, substantially homogenous axial magnetic field within said conduit having a gradient along the direction of flow of said fluid sufficient to induce nuclear paramagentization in said fluid;

applying to a region within said conduit a radio frequency pulse having a first frequency about equal to the Larmor precession frequency of the nuclei of said element at the field intensity of said first magnetic field, whereby to generate a free induction decay signal and whereby to alter the nuclear magnetization within a bolus of said fluid to thereby tag said bolus with respect to fluid preceding and following said bolus;

applying a series of 180° radio frequency pulses to said conduit region within a time less than the spin-lattice relaxation time of said nuclear magnetic resonance, whereby to generate a series of spin echo signals;

measuring the frequency of said spin echo signals over predetermined periods of time to obtain for each period of time the mean instantaneous frequency of said nuclear magnetic resonance; and deriving the velocity of said fluid from the rate of change of said mean instantaneous spin echo frequency.

4. A method for measuring flow of fluid in a conduit, the atomic nuclei of at least one component of said fluid displaying a nuclear magnetic moment and angular momentum, comprising the steps of:

(a) establishing a first static, substantially homogenous axial magnetic field within said conduit having a gradient along the direction of flow of said fluid sufficient to induce nuclear paramagnetization in said fluid;

(b) applying to a region within said conduit a radio frequency pulse having a first frequency about equal to the Larmor precession frequency of the nuclei of said element at the field intensity of said first magnetic field, whereby to generate a free induction decay signal and whereby to alter the nuclear magnetization within a bolus of said fluid to thereby tag said bolus with respect to fluid preceding and following said bolus;

(c) applying a 180° radio frequency pulse to said conduit region to generate a spin echo signal;

(d) measuring the maximum amplitude of said spin echo signal;

(e) when said maximum amplitude is equal to or above a predetermined thershold level, measuring the frequency of said spin echo signal over a predetermined period of time to obtain for that period the mean instantaneous frequency of said nuclear magnetic resonance, deriving the velocity of said fluid from the rate of change of said mean instantaneous spin echo frequency from said pervious spin echo measurement, and returning to step (c);

(f) when said maximum amplitude is less than said predetermined thershold level, determining from previous measurements the average fluid velocity of said fluid from the beginning of free induction decay of said nuclear magnetic resonance to the present, determining the maximum time period as between (i) the time required for full free induction decay of said nuclear magnetic resonance and (ii) the time for said fluid to flow at said average fluid velocity a distance equal to the thickness of said bolus in the direction of said first magnetic field, and when time lapse from beginning of free induction decay of the nuclear magnetic resonance is greater than said maximum time period, reapplying to said conduit a radio frequency pulse chosen to generate a free induction decay signal.

5. The method of claims 1, 2, 3 or 4 including the sequential steps of:
   establishing a second static, magnetic field gradient orthogonal to the first magnetic field gradient and applying thereto a paramagnetizing radio frequency pulse; and subsequently
   establishing a third static magnetic field gradient orthogonal to the first and the second magnetic field gradients and applying thereto a paramagnetizing radio frequency pulse;
   whereby to select a volume within said bolus from which said fluid flow is measured.

6. The method of claim 1, 2, 3 or 4 in which said gradient increases axially in the direction of flow of said fluid.

7. The method of claim 5 in which the gradient of said first magnetic field increases axially in the direction of flow of said fluid and the gradient of said second and third magnetic fields increase axially outwardly from their point of mutual orthogonal crossing.

8. The method of claim 1 in which said conduit comprises a a blood vessel and said fluid component is hydrogen proton.

9. A method for measuring the flow of blood in a blood vessel, comprising the steps of:
   (a) establishing a plurality of sequential static, axial magnetic field gradients across said blood vessel having gradients increasing axially outwardly along three orthogonal axes, the first field having a gradient vector collinear with, and increasing along, the desired direction of flow measurement of said blood;
   (b) applying to each said established magnetic field a radio frequency pulse having a frequency about equal to the Larmor precession frequency of the nuclei of hydrogen proton at the field intensity of the respective magnetic field, whereby to alter the nuclear magnetization within a selected volume of said blood to thereby tag said volume with respect to blood preceding and following said volume and generate a free induction decay signal;
   (c) measuring the free induction decay signal over predetermined periods of time to obtain for each period of time the mean instantaneous frequency of the nuclear magnetic resonance of said hydrogen protons;
   (d) deriving the velocity of said blood from the rate of change of said mean instantaneous frequency;
   (e) when magnetization of said volume reaches a static value, returning to step (a); and
   (f) until magnetization of said volume has reached a static value, conducting a series of steps, comprising:
      (1) applying a 180° radio frequency pulse to said selected volume to generate a spin echo signal;
      (2) measuring the maximum amplitude of said spin echo signal and its mean instantaneous frequency over a predetermined period of time;
      (3) when said maximum amplitude is equal to or above a predetermined thershold level, obtaining from the rate of change of the mean instantaneous frequency of said nuclear magnetic resonance, the velocity of said blood and returning to step (f) (1);
      (4) when said maximum amplitude is less than said predetermined threshold level, determining from previous measurements the average velocity of said blood from the beginning of free induction decay of said nuclear magnetic resonance to the present, determining the maximum time period as between (i) the time required for full free induction decay of said nuclear magnetic resonance and (ii) the time for said blood to flow at said average blood velocity a distance equal to the thickness of said volume in the direction of said first magnetic field, and if time lapse from beginning to free induction decay of said nuclear magnetic resonance is less than said maximum time period then waiting, else returning to step (a).

10. Apparatus for measuring flow of fluid in a conduit, the atomic nuclei of at least one component of said fluid displaying a nuclear magnetic moment and angular momentum, comprising:
    means establishing a first static, substantially homogenous axial magnetic field about said conduit whereby a gradient along the direction of flow of said fluid is obtainable sufficient to induce nuclear paramagnetization in said fluid;
    means for applying to a region within said conduit a radio frequency pulse chosen to alter the nuclear magnetization within a bolus of said fluid to thereby tag said bolus with respect to fluid preceding and following said bolus;
    means for measuring the frequency of nuclear magnetic resonance of the atomic nuclei of said element in said bolus over predetermined periods of time to obtain for each period of time the means instantaneous frequency of said nuclear magnetic resonance; and
    means for deriving the velocity of said fluid from the rate of change of said mean instantaneous frequency.

11. Apparatus for measuring flow of fluid in a conduit, the atomic nuclei of at least one component of said fluid displaying a nuclear magnetic moment and angular momentum, comprising:
    means for establishing first, second and third orthogonally related, static axial magnetic fields, each being substantially homogenous;
    means for placing said conduit within said fields whereby a gradient along the direction of flow of said fluid is obtainable sufficient to induce nuclear paramagnetization in said fluid;
    means for applying to said fields radio frequency pulses chosen to alter the nuclear magnetization of a selected volume within a bolus of said fluid to thereby generate a free induction decay signal and tag said bolus with respect to fluid preceding and following said bolus;

means for measuring the frequency of nuclear magnetic resonance of the atomic nuclei of said element in said bolus over predetermined periods of time to obtain for each period of time the mean instantaneous frequency of said nuclear magnetic resonance; and means for deriving the velocity of said fluid from the rate of change of said mean instantaneous frequency.

12. Apparatus for measuring flow of fluid in a conduit, the atomic nuclei of at least one component of said fluid displaying a nuclear magnetic moment and angular momentum, comprising:

means for establishing a first static, substantially homogenous axial magnetic field;

means for placing said conduit within said field whereby a gradient along the direction of flow of said fluid is obtainable sufficient to induce nuclear paramagnetization in said fluid;

means for applying to a region within said conduit a radio frequency pulse chosen to alter the nuclear magnetization within a bolus of said fluid to thereby generate a free induction decay signal and tag said bolus with respect to fluid preceding and following said bolus; and feedback control means for:

(a) applying a 180° radio frequency pulse to said conduit region to generate a spin echo signal;

(b) measuring the maximum amplitude of said spin echo signal;

(c) when said maximum amplitude is equal to or above a predetermined threshold level, measuring the frequency of said spin echo signal over a predetermined period of time to obtain for that period the mean instantaneous frequency of said nuclear magnetic resonance, if a previous spin echo measurement was made then deriving the velocity of said fluid from the rate of change of said mean instantaneous spin echo frequency from said previous spin echo measurement, and returning to step (a);

(d) when said maximum amplitude is less than said predetermined thershold level, determining from previous measurements the average fluid velocity of said fluid from the beginning of free induction decay of said nuclear magnetic resonance to the present, determining the maximum time period as between (i) the time required for full free induction decay of said nuclear magnetic resonance and (ii) the time for said fluid to flow at said average fluid velocity a distance equal to the thickness of said bolus in the direction of said first magnetic field, and when time lapse from beginning of free induction decay of the nuclear magnetic resonance is greater than said maximum time period, reapplying to said conduit a radio frequency pulse chosen to generate a free induction decay signal.

13. Apparatus for measuring flow of fluid in a conduit, the atomic nuclei of at least one component of said fluid displaying a nuclear magnetic moment and angular momentum, comprising:

means for establishing first, second and third orthogonally related, static axial magnetic field, each being substantially homogenous;

means for placing said conduit within said fields whereby a gradient along the direction of flow of said fluid is obtainable sufficient to induce nuclear paramagnetization in said fluid;

means for applying to said fields radio frequency pulses chosen to alter the nuclear magnetization of a selected volume within a bolus of said fluid to thereby generate a free induction decay signal and tag said bolus with respect to fluid preceding and following said bolus;

feedback control means for:

(a) applying a 180° radio frequency pulse to said conduit region to generate a spin echo signal;

(b) measuring the maximum amplitude of said spin echo signal;

(c) when said maximum amplitude is equal to or above a predetermined threshold level, measuring the frequency of said spin echo signal over a predetermined period of time to obtain for that period the mean instantaneous frequency of said nuclear magnetic resonance, if a previous spin echo measurement was made then deriving the velocity of said fluid from the rate of change of said mean instantaneous spin echo frequency from said previous spin echo measurement, and returning to step (a);

(d) when said maximum amplitude is less than said predetermined threshold level, determining from previous measurements the average fluid velocity of said fluid from the beginning of free induction decay of said nuclear magnetic resonance to the present, determining the maximum time period as between (i) the time required for full free induction decay of said nuclear magnetic resonance and (ii) the time for said fluid to flow at said average fluid velocity a distance equal to the thickness of said bolus in the direction of said first magnetic field, and when time lapse from beginning of free induction decay of the nuclear magnetic resonance is greater than said maximum time period, reapplying to said conduit a radio frequency pulse chosen to generate a free induction decay signal.

14. Apparatus for measuring flow of fluid in a conduit, the atomic nuclei of at least one component of said fluid displaying a nuclear magnetic moment and angular momentum, comprising:

means for establishing a first static, substantially homogenous axial magnetic field;

means for placing said conduit within said field whereby a gradient along the direction of flow of said fluid is obtainable sufficient to induce nuclear paramagentization in said fluid;

means for applying to a region within said conduit a radio frequency pulse chosen to alter the nuclear magnetization within a bolus of said fluid to thereby generate a free induction decay signal and tag said bolus with respect to fluid preceding and following said bolus; and feedback control means for:

(a) measuring free induction decay signals over predetermined periods of time to obtain for each period of time the mean instantaneous frequency of the nuclear magnetic resonance of said fluid;

(b) deriving the velocity of said fluid from the rate of change of said mean instantaneous frequency;

(c) when magnetization of said volume reaches a static value, reinstating the application of radio frequency pulse selected to generate a free induction decay signal; and (d) until magnetization of said volume has reached a static value, conducting a series of steps, comprising:
  (1) applying a 180° radio frequency pulse to generate a spin echo signal;
  (2) measuring the maximum amplitude of said spin echo signal and its mean instantaneous frequency over a predetermined period of time;
  (3) when said maximum amplitude is equal to or above a predetermined threshold level, obtaining from the rate of change of the mean instantaneous frequency of said nuclear magnetic resonance the velocity of said fluid, and returning to step (d) (1);
  (4) when said maximum amplitude is less than said predetermined thershold level, determining from previous measurements the average velocity of said fluid from the beginning of free induction decay of said nuclear magnetic resonance to the present, determining the maximum time period as between (i) the time required for full free induction decay of said nuclear magnetic resonance and (ii) the time for said fluid to flow at said average fluid velocity a distance equal to the thickness of said volume in the direction of said first magnetic field, and if time lapse from beginning of free induction decay of said nuclear magnetic resonance is less than said maximum time period then waiting, else returning to step (a).

15. Apparatus for measuring flow of fluid in a conduit, the atomic nuclei of at least one component of said fluid displaying a nuclear magnetic moment and angular momentum:, comprising:
  means for establishing first, second and third or orthogonally related, static axial magnetic fields, each being substantially homogenous;
  means for placing said conduit within said field whereby a gradient along the direction of flow of said fluid is obtainable sufficient to induce nuclear paramagnetization in said fluid;
  means for applying to said fields radio frequency pulses chosen to alter the nuclear magnetization of a selected volume within a bolus of said fluid to thereby generate a free induction decay signal and tag said bolus with respect to fluid preceding and following said bolus;
feedback control means for:
(a) measuring free induction decay signals over predetermined periods of time to obtain for each period of time the mean instantaneous frequency of the nuclear magnetic resonance of said fluid;
(b) deriving the velocity of said fluid from the rate of change of said mean instantaneous frequency;
(c) when magnetization of said volume reaches a static value reinstating the application of radio frequency pulse selected to generate a free induction decay signal; and
(d) until magnetization of said volume has reached a static value, conducting a series of steps, comprising:
  (1) applying a 180° radio frequency pulse to generate a spin echo signal;
  (2) measuring the maximum amplitude of said spin echo signal and its mean instantaneous frequency over a predetermined period of time;
  (3) when said maximum amplitude is equal to or above a predetermined threshold level, obtaining from the rate of change of the mean instantaneous frequency of said nuclear magnetic resonance the velocity of said fluid, and returning to step (d) (1);
  (4) when said maximum amplitude is less than said predetermined threshold level, determining from previous measurements the average velocity of said fluid from the beginning of free induction decay of said nuclear magnetic resonance to the present, determining the maximum time period as between (i) the time required for full free induction decay of said nuclear magnetic resonance and (ii) the time for said fluid to flow at said average fluid velocity a distance equal to the thickness of said volume in the direction of said first magnetic field, and if time lapse from beginning of free induction decay of said nuclear magnetic resonance is less than said maximum time period then waiting, else returning to step (a).

* * * * *